United States Patent [19]

Robert et al.

[11] 4,397,865
[45] Aug. 9, 1983

[54] METHOD FOR PREVENTING RENAL PAPILLARY NECROSIS WITH PROSTAGLANDINS

[75] Inventors: André Robert, Kalamazoo; George A. Elliott, Portage, both of Mich.

[73] Assignee: The Upjohn Company, Kalamazoo, Mich.

[21] Appl. No.: 433,587

[22] Filed: Oct. 12, 1982

[51] Int. Cl.³ .................... A61K 31/19; A61K 31/215
[52] U.S. Cl. .................................... 424/317; 424/274; 424/305; 424/319; 424/273 R
[58] Field of Search .............. 424/305, 317, 319, 274, 424/273 R

[56] References Cited

PUBLICATIONS

Chem. Abst., 10th Coll., General Subject, vol. 86-95, (1977-1981), pp. 19431GS to 19462GS.
Chem. Abst., 10th Coll., Chemical Index, vol. 86-95, (1977-1981), pp. 8684cs and 8685cs.

Primary Examiner—Sam Rosen
Attorney, Agent, or Firm—Lawrence T. Welch

[57] ABSTRACT

The present invention provides a method for the prevention of renal papillary necrosis induced by non-steroidal anti-inflammatory compounds (NOSAC) comprising the administration of certain prostaglandins.

5 Claims, No Drawings

METHOD FOR PREVENTING RENAL PAPILLARY NECROSIS WITH PROSTAGLANDINS

DESCRIPTION

BACKGROUND OF THE INVENTION

The present invention provides a new use for some known compounds. More particularly, the present invention provides a method for preventing renal papillary necrosis induced by non-steroidal anti-inflammatory compounds (NOSAC) by the administration of certain prostaglandins.

Renal papillary necrosis is a condition of the kidneys which is associated with the administration of NOSAC. Originally, renal papillary necrosis was thought to be a form of fulminating pyelonephritis. See, e.g., Morales, et al., Arch. Surg. 103:420 (1971). However, it has also been found to be associated with the administration of various analgesic compounds. See, Spuhler, et al., Z. Klin. Med. 151:1-50 (1953). Renal papillary necrosis is characterized by morpholosical changes and renal failure as a consequence of damage to the renal papillae. Renal papillary necrosis has been associated with phenylbutazone (see Morales, supra); phenacetin (see, e.g., Burry, et al., Med. J. Aust., 1:31-36 (1974)); indomethacin (Arnold, et al., Pathology 6:303-313 (1974)), aspirin (see Arnold, supra); amidopyrine (see Arnold, supra) and the like. Renal papillary necrosis is thus a serious problem associated with the administration of non-steroidal anti-inflammatory compounds.

The prostaglandins are derivatives of prostanoic acid, having the carbon atom numbering and structure as shown in Formula I. A trivial system of nomenclature has been devised, which classifies the prostaglandins according to these substituents on the cyclopentane ring. See, N. A. Nelson, Journal of Medicinal Chemistry, 17:911 (1974). For a discussion of the uses of the prostaglandins, see, e.g., N. A. Nelson, et al., Chemical and Engineering News, pp. 30-44 (Aug. 16, 1982).

Pharmacological agents which prevent necrotic changes in cells are known as cytoprotective agents. Numerous gastrointestinal cytoprotective effects of the prostaglandins are known. See for example, U.S. Pat. No. 4,083,998 (Robert, "Treatment of Inflammatory Disease of the Mammalian Large Intestine with Cytoprotective Prostaglandins"), issued Apr. 11, 1978, U.S. Pat. No. 4,081,553 (Robert, Cytoprotective Prostaglandins for Use in Intestinal Diseases"), issued Mar. 28, 1978, and U.S. Pat. No. 4,097,603 (Robert, "Gastric Cytoprotection with Non-Antisecretory Doses of Prostaglandins"), issued June 27, 1978.

PRIOR ART $PGE_2$ has been shown to protect against renal failure due to glycerol in saline loaded rats. See, Papanicolaou, et al., Clin. Sci. Mol. Med. 49:507 (1975). Ruwart, et al., discloses that 16,16-dimethyl $PGE_2$ protects the kidney from damage induced by carbon tetrachloride and ANIT ($\alpha$-naphthylisothiocyanate). See, Prostaglandins, 21 (Supplement):97-102 (1981). Certain prostaglandins are known to be useful for the prevention of gastrointestinal side effects from NOSAC administration. See, e.g., U.S. Pat. No. 3,917,828.

SUMMARY OF THE INVENTION

The present invention particularly provides: a method for the prevention of renal papillary necrosis induced by non-steroidal antiinflammatory compounds (NOSAC) in a mammal susceptible to said necrosis comprising systemically administering to said mammal an amount of a renal cytoprotective prostaglandin effective to prevent said necrosis.

In accomplishing the purposes of this invention those compounds which are useful as renal cytoprotective prostaglandins are those prostaglandins or prostaglandin analogs which are at least one percent as potent as 16,16-dimethyl-$PGE_2$ in effecting a reduction in renal papillary necrosis induced by mefenamic acid in the standard laboratory test set forth in Example 1.

Thus, 16,16-dimethyl-$PGE_2$ and 16,16-dimethyl-$PGF_{2\alpha}$ are preferred compounds to be employed in the method of this invention. Other prostaglandins which are also useful for this purpose include those prostaglandins that exert a cytoprotective effect on gastrointestinal tract, as described, e.g., in U.S. Pat. Nos. 3,917,828; 4,081,553; and 4,097,603.

An important aspect of this invention is the determination of subjects who are particularly susceptible to the acquisition of renal papillary necrosis. Such subjects include mammals, especially humans, who are receiving high doses of a particular NOSAC which is known to be particularly potent in causing renal papillary necrosis and who are not receiving other cytoprotective prostaglandin therapy.

A well known side-effect of NOSAC administration is the development of gastric lesions and gastrointestinal distress. These gastrointestinal side-effects from NOSAC administration stem from the fact that NOSAC are prostaglandin synthetase inhibitors. Among the NOSAC agents which are prostaglandin synthetase inhibitors are indomethacin, aspirin, phenylbutazone, mefenamic acid, flufenamic acid, naproxen, 2-phenoxyphenylpropionic acid, (+)-3-chloro-4-cyclohexyl-$\alpha$-methylphenylacetic acid, and ibuprofen. For a description of the use of prostaglandins to prevent the gastrointestinal side-effects of NOSAC administration, see, e.g., U.S. Pat. No. 3,917,828.

However, the gastrointestinal side-effects of NOSAC administration are not experienced by approximately half of the subjects who receive such treatment. Thus, for example, many patients who are receiving large dosages of NOSAC for anti-arthritic purposes do not experience any gastrointestinal distress. Many of these patients may, however, be at risk for renal papillary necrosis. Persons in this class are prime subjects for the method of the present invention.

The current state of medical knowledge does not permit the precise prediction of persons particularly susceptible to renal papillary necrosis. However, all persons receiving NOSAC therapy are at risk for renal papillary necrosis. Also at risk are persons receiving NOSAC therapy who have a history of kidney disease, kidney injury, and the like.

Mammals susceptible to renal papillary necrosis induced by nonsteroidal anti-inflammatory compounds include any mammal undergoing NOSAC therapy who is determined to be at risk based on the factors noted above. More preferred are mammals undergoing NOSAC therapy with a compound which is particularly potent in inducing renal papillary necrosis. Still more preferred are mammals receiving a NOSAC which is particularly potent in causing renal papillary necrosis who are not experiencing gastrointestinal side-effects and are thus not receiving cytoprotective prostaglandin therapy. The method of the present invention is best employed prophylactically by administering renal cytoprotective prostaglandins to all persons who are at risk.

Agents which are particularly potent in causing renal papillary necrosis experimentally include:
Fenoprofen;
Ibuprofen;
Flurbiprofen;
Indomethacin;
Mefenamic acid;
Naproxen; and
Phenylbutazone.

The present invention includes the treatment of each of various mammalian species, including humans. Humans are the most preferred subjects for the method of the present invention. With respect to non-humans, the present invention is particularly and especially concerned with treating domesticated animals, for example, cattle, horses, dogs, cats and swine. By prevention is meant partial to total avoidance of kidney damage due to renal papillary necrosis.

Any convenient route of administration is employed. Thus, oral formulation and oral administration is, for example, the preferred route for use in humans although parenteral (e.g., intravenous, intraperitoneal, and intramuscular) administration is also employed. See, e.g., U.S. Pat. No. 3,903,297 (Robert, "Method of Treatment in Prophylaxis of Gastric Hypersecretion in Gastric Acid and Duodenum Ulcers Using Prostaglandin Analogs"), issued Sept. 2, 1975, columns 6-16 for some appropriate and well known means of administering the prostaglandins discussed herein.

The dosage regimen for the renal cytoprotective prostaglandin in accord with this invention will depend on a variety of factors, including the type, age, weight, sex, and medical condition of the mammal, the dosage regimen of the NOSAC, the kind of NOSAC administered, renal cytoprotective prostaglandin to be administered. It is within the skill of the attending physician or veterinarian to determine the class of subjects who are at risk for renal papillary necrosis and to prescribe an effective amount of the renal cytoprotective prostaglandin to prevent renal papillary necrosis. In doing that, the physician or veterinarian would by one method start at a relatively low dose of the renal cytoprotective prostaglandin, for example, about 0.25 mg/kg/day to about 0.1 µg/kg, day, and observe the response of the human or animal patient for a few days. The dose of the renal cytoprotective prostaglandin is then adjusted downward or upward until the maximum effective dose is found. For example, the maximum needed dose is usually between about 25 mg/kg/day and about 15 µg/kg/day although it may be necessary to occasionally exceed these doses when the renal side effects of NOSAC therapy are especially severe. Once the minimum effective dose of the particular renal cytoprotective prostaglandin is determined for a particular subject, it is advantageous to provide the subject with the dosage schedule which will provide a substantially uniform level of renal cytoprotective prostaglandin to the kidney.

The renal cytoprotective prostaglandins disclosed herein are well known and readily available compounds. Thus, 16,16-dimethyl-$PGE_2$ is disclosed in U.S. Pat. No. 3,903,131 and 16,16-dimethyl-$PGF_{2\alpha}$ is disclosed in U.S. Pat. No. 3,954,833.

DESCRIPTION OF THE PREFERRED EMBODIMENTS

The present invention is seen more fully by the example given below.

EXAMPLE 1

Single oral doses of mefenamic acid, a non-steroidal anti-inflammatory compound (NOSAC), were given to rats over a dose range previously shown to produce renal papillary necrosis (RPN). Two prostaglandins, 16,16-dimethyl-$PGE_2$ and 16,16-dimethyl $PGF_{2\alpha}$ were given orally by stomach tube twice daily for 4 days beginning one hour before mefenamic acid administration. Doses of 800 and 1250 mg/kg of mefenamic acid and 0.2 mg/kg of 16,16-dimethyl-$PGE_2$ and 10 mg/kg of 16,16-dimethyl $PGF_{2\alpha}$ were used.

Single oral doses of 800 mg/kg of mefenamic acid produced RPN in all rats. The incidence was reduced to 40% by 16,16-dimethyl $PGE_2$ ($P<0.01$) and to 56% by 16,16-dimethyl $PGF_{2\alpha}$ ($P<0.05$). At a dose of 1250 mg/kg of mefenamic acid, 45% of the animals died. Mortality was reduced to 18% in the groups given this dose of mefenamic acid plus either of the prostaglandins. The incidence of RPN was reduced from 91% (1250 mg/kg of mefenamic acid alone) to 73% (NS) and 55% (NS) when given mefenamic acid plus either 16,16-dimethyl-$PGE_2$ or 16,16-dimethyl $PGF_{2\alpha}$, respectively. The intestinal lesions characteristic of NOSAC treatment (jejuno-ileal ulcers) produced by both dose levels of mefenamic acid were almost completely prevented by the two prostaglandins.

The results are summarized in Table I. As can be seen, both prostaglandins significantly decreased the incidence of renal papillary necrosis induced by mefenamic acid.

TABLE 1
Treatment Regimens and Results

| Treatment | All Animals RPN Incidence | Survivors Only RPN Incidence | % RPN |
|---|---|---|---|
| Regimen 1 (Preliminary Study) | | | |
| Untreated | 0/3 | 0/3 | 0 |
| 1600 mg/kg MA | 10/10 | 4/4 | 100 |
| 1600 mg/kg MA + 0.1 mg/kg $PGE_2$ | 5/6 | 2/3 | 67 |
| 1600 mg/kg MA + 5 mg/kg $PGF_{2\alpha}$ | 5/6 | 5/5 | 100 |
| 2500 mg/kg MA | 9/10 | 0 | |
| 2500 mg/kg MA + 0.1 mg/kg $PGE_2$ | 3/6 | 0 | |
| 2500 mg/kg MA + 5 mg/kg $PGF_{2\alpha}$ | 6/6 | 0 | |
| Regimen 2 | | | |
| Vehicle #122 + 5% ethanol | 0/11 | 0/11 | 0 |
| 800 mg/kg MA + 5% ethanol | 11/11 | 10/10 | 100 |
| 800 mg/kg MA + $PGE_2$ (0.2 mg/kg) | 4/11 | 4/10 | 40 |
| 800 mg/kg MA + $PGF_{2\alpha}$ (10 mg/kg) | 6/11 | 6/11 | 55 |
| 1250 mg/kg MA + 5% ethanol | 10/11 | 6/6 | 100 |
| 1250 mg/kg MA + $PGE_2$ (0.2 mg/kg) | 8/11 | 7/9 | 78 |
| 1250 mg/kg MA + $PGF_{2\alpha}$ (10 mg/kg) | 6/11 | 5/9 | 56 |
| Vehicle #122 + $PGE_2$ (0.2 mg/kg) | 0/11 | 0/11 | 0 |
| Vehicle #122 + $PGF_{2\alpha}$ (10 mg/kg) | 0/11 | 0/11 | 0 |

MA = mefenamic acid
$PGE_2$ = 16,16-dimethyl-$PGE_2$
$PGF_{2\alpha}$ = 16,16-dimethyl-$PGF_{2\alpha}$
Vehicle #122 = 0.25% methylcellulose solution
Prostaglandins administered in 5% ethanol, mefenamic acid administered in vehicle #122. Administration was by stomach tube.

We claim:
1. A method for the prevention of renal papillary necrosis induced by non-steroidal anti-inflammatory compounds (NOSAC) in a mammal susceptible to said necrosis comprising systemically administering to said mammal an amount of a renal cytoprotective prostaglandin effective to prevent said necrosis.

2. A method of claim 1, wherein said mammal is not susceptible to NOSAC-induced gastrointestinal side effects.

3. A method of claim 2, wherein said mammal is a human.

4. A method of claim 3, wherein the renal cytoprotective prostaglandin is 16,16-dimethyl-$PGE_2$.

5. A method of claim 3, wherein the renal cytoprotective prostaglandin is 16,16-dimethyl $PGF_2\alpha$.

* * * * *